United States Patent [19]

KenKnight et al.

[11] Patent Number: 5,391,200
[45] Date of Patent: Feb. 21, 1995

[54] DEFIBRILLATION PATCH ELECTRODE HAVING CONDUCTOR-FREE RESILIENT ZONE FOR MINIMALLY INVASIVE DEPLOYMENT

[75] Inventors: Bruce H. KenKnight, Minneapolis; Jeffrey A. Hall, Bloomington, both of Minn.

[73] Assignee: Cardiac Pacemakers, Inc., St. Paul, Minn.

[21] Appl. No.: 209,356

[22] Filed: Mar. 10, 1994

Related U.S. Application Data

[63] Continuation of Ser. No. 954,616, Sep. 30, 1992, abandoned.

[51] Int. Cl.⁶ .............................................. A61N 1/05
[52] U.S. Cl. .................................. 607/129; 128/642
[58] Field of Search .................. 128/639, 642, 644; 607/129, 132, 142, 149, 152

[56] References Cited

U.S. PATENT DOCUMENTS

| | | | |
|---|---|---|---|
| 2,536,271 | 1/1951 | Fransen | 128/804 X |
| 3,380,445 | 4/1968 | Frasier | 128/639 |
| 4,144,889 | 3/1979 | Tyers et al. | |
| 4,233,987 | 11/1980 | Feingold | 128/639 |
| 4,827,932 | 5/1989 | Ideker et al. | 128/784 X |
| 4,938,231 | 7/1990 | Milijasevic et al. | 128/785 X |
| 5,042,463 | 8/1991 | Lekholm | 128/642 X |
| 5,154,182 | 10/1992 | Muaddeb | 128/784 |

FOREIGN PATENT DOCUMENTS

| | | |
|---|---|---|
| 0211166A2 | 2/1987 | European Pat. Off. . |
| 0460324A2 | 12/1991 | European Pat. Off. . |
| 0461539 | 12/1991 | European Pat. Off. ............ 128/784 |
| WO89/05168 | 6/1989 | WIPO . |
| WO92/09330 | 6/1992 | WIPO . |

*Primary Examiner*—Angela D. Sykes
*Attorney, Agent, or Firm*—Keck, Mahin & Cate

[57] ABSTRACT

A cardioversion/defibrillation electrode comprising an insulative element which supports one or more planar conductive elements. The conductive elements are spaced apart from each other by a "conductor-free" region, which serves as a spring loaded hinge about which the electrode may preferentially bend. The electrode is thereby spring loaded to adopt a substantially planar orientation in a relaxed state but is capable of bending to a non planar orientation wherein the electrode is folded about the hinge to facilitate intrathoracic introduction. After introduction, the spring loaded hinge causes the electrode to adopt its relaxed substantially planar orientation for attachment on or near the heart surface. Due to the preferential bending in the "conductor-free" region, the electrode conductive elements are not permanently or substantially deformed during implantation.

14 Claims, 3 Drawing Sheets

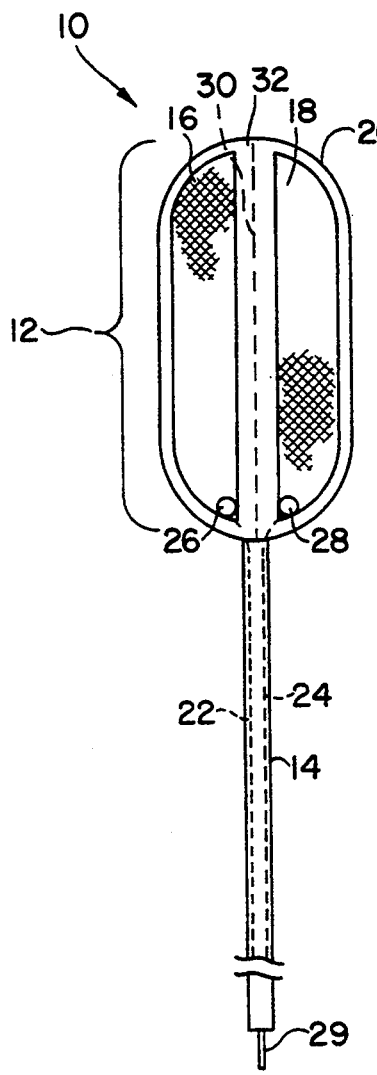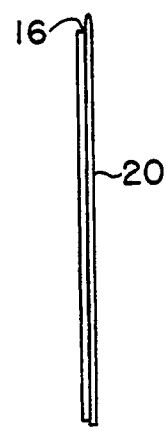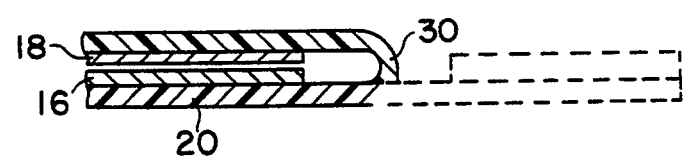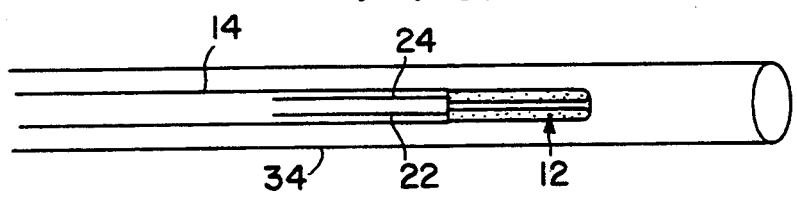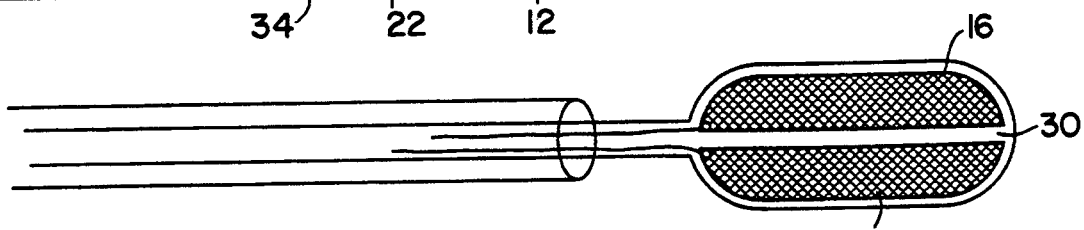
FIG. 1
FIG. 2
FIG. 3
FIG. 4
FIG. 5

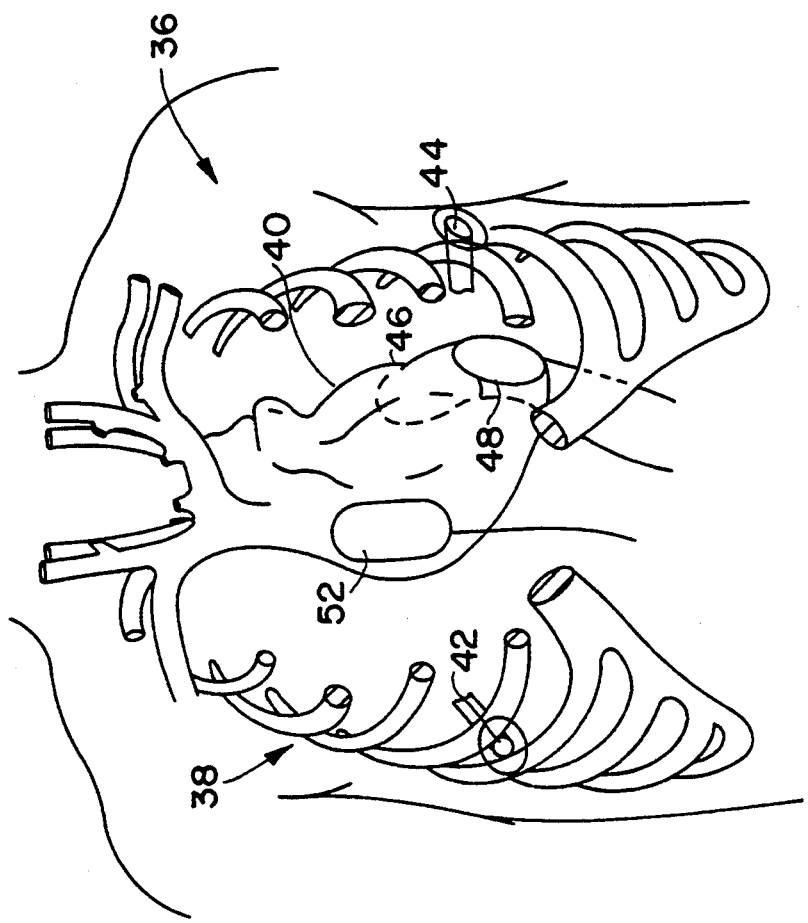
FIG. 14
FIG. 13
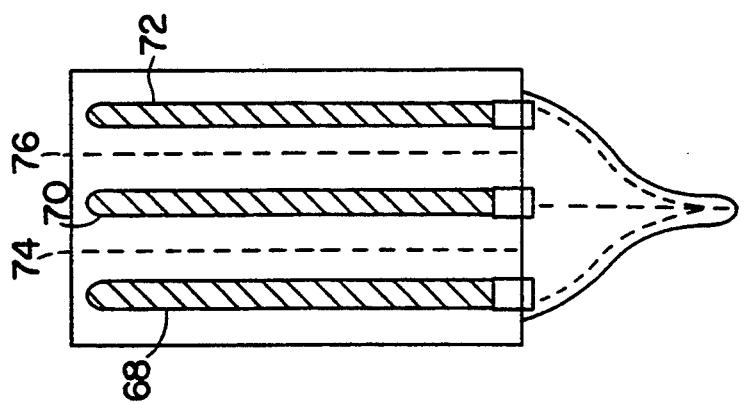
FIG. 11
FIG. 12

DEFIBRILLATION PATCH ELECTRODE HAVING CONDUCTOR-FREE RESILIENT ZONE FOR MINIMALLY INVASIVE DEPLOYMENT

This application is a continuation of U.S. patent application Ser. No. 954,616, filed Sep. 30, 1992, now abandoned.

This application is related to U.S. patent application Ser. No. 07/954,514 filed concurrently herewith and entitled: Method and Applicator Tool for Implanting Cardiac Defibrillation Electrodes.

BACKGROUND OF THE INVENTION

The present invention relates to a cardioversion/defibrillation electrode and more particularly to a patch electrode having an improved structure to simplify implantation procedures and to preserve the structural integrity of the electrode after implantation.

In the field of cardioversion/defibrillation, electrodes are mounted in, on or about the heart to discharge and generate an electric field which is capable of terminating potentially lethal tachyarrhythmias. The electrodes come in various forms, including endocardial catheter electrodes, epicardial patch electrodes, and subcutaneous electrodes. A conventional patch electrode such as shown in U.S. Pat. No. 4,291,707—Heilman et al is designed to attach on or near the heart surface and is generally a thin planar device having a lead extending therefrom which connects electrically conductive surfaces on the electrode with a source of electrical energy, typically embodied as an implantable pulse generator.

The patch electrode includes conductive surfaces on the side designed to face the heart. These conductive surfaces may take on a variety of shapes and sizes. One type of conductive element useful on a patch electrode is a conductive mesh. The conductive mesh is attached to an insulative backing material and is connected to insulated electrically conductive leads. To adapt to the changing surfaces of the heart during cardiac contractions and to facilitate implantation into the thoracic region, some patch electrodes have been designed with a degree of flexibility.

A problem with patch electrodes heretofore known is that during intrathoracic introduction procedures, the electrode must be bent and contorted to achieve proper placement on or about the heart. Consequently, the conductive mesh on the electrode is subject to a bending stress which may exceed the mesh material yield stress, with the result that it may become permanently deformed after the introduction procedure. The permanently deformed electrode may not function properly since the conductive mesh no longer conforms optimally to the generally curved surfaces of the epicardium.

U.S. Pat. No. 5,042,463—Lekholm et al discloses several embodiments of a flexible, planar patch electrode for defibrillation in which there are "conductor-free" zones in which the patch could be folded without deforming the electrode conductor. However, in these "conductor-free" zones the insulative backing is removed, such that the electrode would not have a resilient spring-like hinge effect that would aid in returning the planar patch to its natural planar state during deployment. Thus, any folding of the planar patch electrode shown in the Lekholm et al patent during an implantation procedure would cause irreparable deformation and possible damage of the electrode conductor in the region of the electrode where the lead portion joins the electrode portion. U.S. Pat. No. 4,827,932—Ideker et al illustrates a large partially bifurcated conformal mesh patch for epicardial defibrillation. However, it teaches contiguous mesh conductive surfaces without regard for the prevention of deformation of the mesh conductive surface. U.S. Pat. No. 4,938,231 Milijasevic depicts an electrode having "conductor-free" zones, but they are in the form of radial slits and semi-circular slots that would prevent folding for improved deployment using minimally invasive techniques.

SUMMARY OF THE INVENTION

It is a primary object of the present invention to provide a cardioversion/defibrillation patch electrode structure which eliminates permanent deformation of the electrode conductive surface after intrathoracic introduction procedures.

Briefly, the present invention relates to a cardioversion/defibrillation electrode designed for implantation on or near the heart surface. The electrode comprises a resilient insulative element which supports one or more electrically conductive surface elements. The conductive surface elements, typically formed of a conductive mesh are spaced apart from each other so as to form a "conductor-free" region or regions, which region or regions serve as a hinge about which the electrode may be bent. The electrode is designed to adopt a substantially planar orientation in a relaxed state but is capable of being bent in the "conductor-free" region to a non-planar orientation wherein the electrode is folded like a hinge to facilitate intrathoracic introduction. After introduction the bent region or regions each act as a spring loaded hinge which causes the electrode to adopt its relaxed substantially planar orientation for attachment on or near the heart surface.

By providing preferential bending regions, and thus controlling the particular manner in which the electrode bends during introduction, the problem of permanent electrode mesh deformation after intrathoracic introduction is eliminated.

The above and other objects and advantages will become more readily apparent when reference is made to the following description taken in conjunction with the accompanying drawings.

BRIEF DESCRIPTION OF THE DRAWINGS

FIG. 1 is a top view of a cardioversion/defibrillation patch electrode and lead constructed in accordance with the present invention.

FIG. 2 is a side view of the electrode shown in FIG. 1.

FIG. 3 is an end view of the electrode of FIG. 1 shown in its folded, spring loaded orientation, and in its relaxed orientation by dashed lines.

FIGS. 4 and 5 are views of the electrode and lead during intrathoracic introduction procedures.

FIG. 11 is a top view of a fourth embodiment of a cardioversion/defibrillation patch electrode and lead constructed in accordance with the present invention.

FIG. 12 is an end view of the fourth embodiment of the cardioversion/defibrillation patch electrode shown in FIG. 11 in its relaxed orientation.

FIG. 13 is an end view of the electrode of FIG. 11 shown in its folded, spring loaded orientation.

FIG. 14 is a perspective view of the thorax of a human body illustrating the heart and the implanted location of the cardioversion/defibrillation patch electrode of this invention.

DETAILED DESCRIPTION OF THE DRAWINGS

Figure 6:
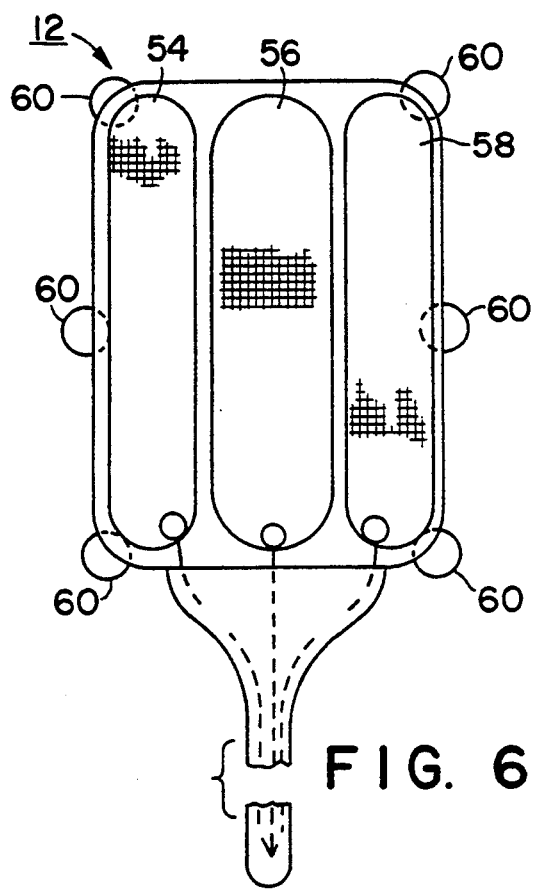
FIG. 6 is a top view of a second embodiment of a cardioversion/defibrillation patch electrode and lead constructed in accordance with the present invention.

Referring first to FIGS. 1 and 2, the cardioversion/defibrillation electrode assembly according to the present invention is generally shown at 10 and comprises a planar conductive electrode portion 12 and a lead member 14. The electrode portion 12 is formed of two or more electrically conductive elements 16 and 18 attached to an electrically insulative and generally mechanically resilient backing element 20. The conductive elements 16 and 18 shown as a wire mesh structure are connected at nodes 26 and 28 respectively to insulated conductors 22 and 24 respectively. The connections at nodes 26 and 28 may be made by well known wire crimping or spot welding processes. The conductors 22 and 24 which are carried inside of lead member 14 are connected in common to a terminal pin 29 at the proximal end of the lead member 14. As is well known in the art, the terminal pin 29 plugs into an implantable pulse generator unit (not shown) for delivery of high strength electrical shocks in the order of 0.1 to 35 Joules.

The mesh elements 16 and 18 are separated from each other on the insulative backing element 20 by a "mesh-free" region 30 which in a preferred embodiment is approximately 1 to 10 millimeters wide. The mesh elements 16 and 18 are substantially coplanar when the backing element 20 is in its natural flat condition. The purpose of the mesh-free region 30 is to provide a "spring loaded" hinge structure to the electrode portion 12 so that the electrode portion 12 may bend, as a hinge, along the dotted line 32, in the mesh-free region 30. This is shown in FIG. 3 where the dashed lines represent the electrode portion 12 in its natural or relaxed orientation and the solid lines represent the electrode portion 12 in its folded, spring loaded orientation. Due to the nature of the insulative backing material and the positioning of the mesh elements, the electrode portion 12 is spring loaded to adopt a planar orientation as shown in FIGS. 1 and 2. An adequate spring force in the mesh-free region is produced by stressing the resilient material. A preferred material for the backing element is Dacron ® reinforced silicone rubber sheeting.

Because the electrode portion is designed to preferentially bend in the region 30, the mesh elements 16 and 18 are not bent. Therefore, there is no deformation of the mesh elements 16 and 18 when the electrode portion is folded for intrathoracic introduction.

FIGS. 4 and 5 illustrate initial and final steps of introducing the electrode 10 into the thoracic region. The electrode portion 12 is folded in the region 30 and inserted into a cannula 34 or other introducing means as shown in FIG. 4. At this point, the electrode portion is in its folded, spring loaded orientation. Once the cannula 34 is positioned near the heart surface, the electrode portion 12 is urged out of the cannula 34. Being then free of the restraint of the cannula 34, it adopts its relaxed planar orientation as shown in FIG. 5. The mesh elements 16 and 18 adopt a substantially flat orientation to facilitate attachment on or near the heart surface.

The electrode according to the present invention may be implanted in any one of several configurations. As an example, one such electrode may be implanted on the high lateral right ventricle and two such electrodes on the left ventricle, one in an anterior and the other in a posterior position. The two left ventricle electrodes are electrically connected in common to form a common anode or cathode.

It is envisioned that the electrode be introduced through a thoracoscopic trocar or a small incision, and thereafter a cannula or other introducing means used to position the electrode on or near the heart surface. Referring to FIG. 14, the thorax 36 of a human body is shown with rib cage 38 and heart 40. A pair of thoracoscopic ports 42 and 44 are shown positioned in the rib cage. These ports, which pass through the chest wall and extend into the thoracic cavity, may be used for introducing and subsequent manipulating and fixing to tissue on or around the heart the patch electrode of this invention. The thoracoscopic ports 42 and 44, which typically have an internal diameter of 10 to 15 millimeters, may be placed in any of several intercostal locations, including those shown in FIG. 14. By way of introduction through the thoracoscopic ports, multiple electrically common electrodes 46 and 48 constructed in accordance with this invention are positioned on the left ventricle. The electrodes 46 and 48 are connected through an adaptor 50 to the negative terminal of an implantable pulse generator unit (not shown). A single electrode 52 is shown positioned on the heart and connected to the positive terminal of an implantable pulse generator unit (not shown).

Larger patch electrodes, having a surface area in the range of 20 to 40 sq. cm. may have more than one mesh-free region so that the electrode may be folded in a "pleated" fashion to decrease the profile of the electrode for introduction.

Figure 7:
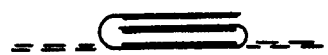
FIG. 7 is an end view of the electrode of FIG. 6 shown in its folded, spring loaded orientation, and in its relaxed orientation by dashed lines.

Referring to FIGS. 6 and 7, an electrode in accordance with this invention with three substantially parallel mesh conductors 54, 56, and 58 is shown. An electrode constructed in this manner has two parallel "conductor-free" zones. Referring to FIG. 7, the electrode of FIG. 6 is shown in its folded or pleated state for deployment using minimally invasive techniques. The dashed lines in FIG. 7 show the unstressed, planar shape of the electrode as it appears in use. As shown in FIG. 6, tabs 60 which extend beyond the border of the electrode portion 12 provide a convenient means of fixation to tissues for electrode immobilization. The tabs are typically formed of Dacron ® reinforced silicone rubber sheeting 0.25 to 1 millimeter thick, or a suitable porous, tissue-in-growth-promoting fabric such as Dacron ®. The tabs are fixed to the tissue by using staples or sutures, either solely or in combination.

While mesh type conductive elements have been illustrated and described with respect to the embodiments of the invention shown in FIGS. 1 through 7, the use of other types of conductive elements is encompassed within the invention. Conductive elements other than mesh which could be used are foils, wires or preferably multi-filer coils (0.5 to 2.5 millimeters major diameter) which are embedded in the insulative backing.

Figure 8:
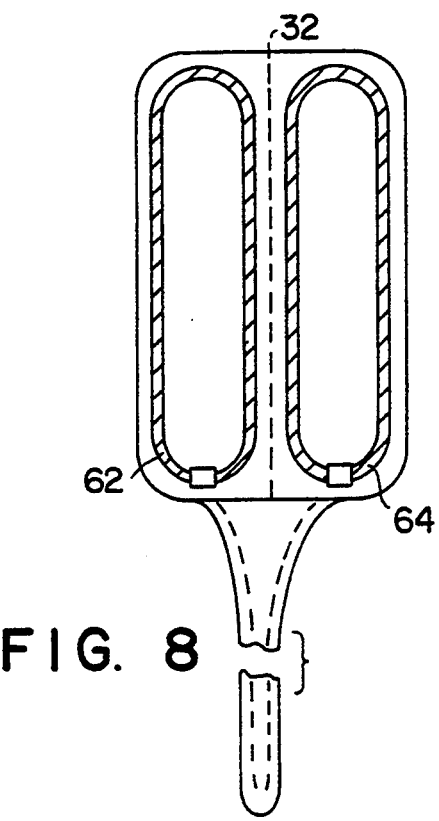
FIG. 8 is a top view of a third embodiment of a cardioversion/defibrillation patch electrode and lead constructed in accordance with the present invention.

FIG. 8 shows a electrode assembly in accordance with this invention wherein two loops 62 and 64 of multi-filer coils are located on either side of a centerline 32 of the backing element 20, along which the electrode assembly may be folded for implantation.

Figure 9:
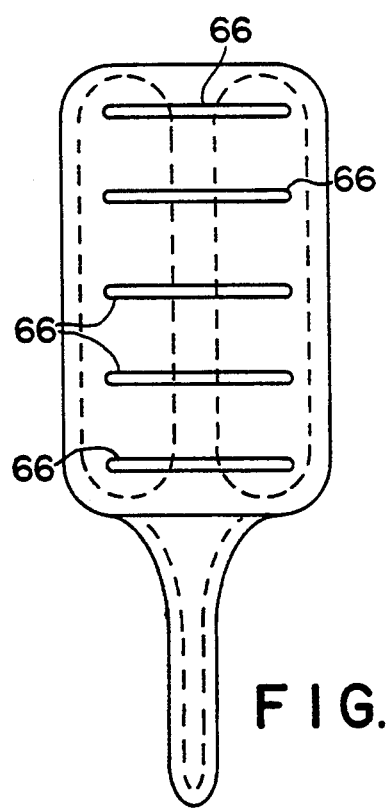
FIG. 9 is a bottom view of the third embodiment of a cardioversion/defibrillation patch electrode shown in FIG. 8.
Figure 10:
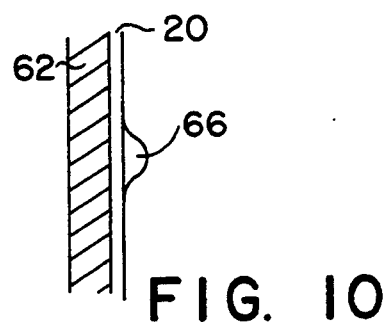
FIG. 10 is a partial cross-sectional side view of the third embodiment of a cardioversion/defibrillation patch electrode shown in FIG. 8.

As shown in FIGS. 9 and 10, the electrode assembly shown in FIG. 8 may be provided with ribs to augment the spring force of the conductor-free zone. The ribs 66 have a height of 1 to 5 times the thickness of the backing element 20 and are placed generally perpendicular to the centerline 32 of the backing element. The ribs 66 are preferably formed of silicone rubber of the same or higher durometer compared to the material of which the backing element 20 is formed and should nominally be two to ten times the backing element 20 thickness in width. The effect of the ribs 66 is to increase the spring-like return force generated by the conductor-free zone. With the use of the ribs, the electrode portion is more forcefully returned to a planar state when the deformation forces of implantation are removed.

FIG. 11 shows still another embodiment of this invention wherein three strands of multi-filer coils are located on the backing element parallel to each other. The patch electrode of FIG. 11 is shown in its relaxed or implanted orientation in FIG. 12, and in the folded or spring loaded orientation in which it is placed during an intrathoracic introduction procedure in FIG. 13.

The above description is intended by way of example only and is not intended to limit the present invention in any way except as set forth in the accompanying claims.

We claim:

1. A cardioversion/defibrillation patch electrode for insertion through a thoracoscopic port comprising::
   an insulative element having first and second opposing surfaces; and at least two electrically conductive elements disposed on said first surface of said insulative element and separated from each other by a conductor-free region of said first surface of said insulative element, said conductor-free region defining a hinge about which the electrode is caused to bend by deformation forces encountered during implantation from a substantially planar orientation in a relaxed state to a folded, springy orientation, said springy orientation causing said electrode to return to said substantially planar configuration when said deformation forces are removed.

2. The electrode of claim 1, wherein said at least two conductive elements are substantially coplanar when the electrode is in the substantially planar orientation.

3. The electrode of claim 2, wherein the electrode may bend through approximately 180 degrees such that said at least two electrically conductive elements are substantially parallel to one another in the folded orientation.

4. The electrode of claim 1, having more than two conductor-free regions separating more than two electrically conductive elements disposed on said first surface.

5. The electrode of claim 1, wherein the electrically conductive elements are formed of a conductive mesh.

6. The electrode of claim 1, wherein the electrically conductive elements are formed of foils.

7. The electrode of claim 1, wherein the electrically conductive elements are formed of multi-filar coils.

8. The electrode of claim 1, wherein at least one rib is provided on said second surface perpendicular to said hinge, to augment the spring force of said conductor-free regions.

9. A cardioversion/defibrillation electrode device for insertion through a thoracoscopic port comprising:
   a lead comprising an elongated insulative member and a plurality of insulated conductors extending through said insulative member;
   an electrode portion connected to said lead comprising:
      an insulative element having first and second opposing surfaces; and
      at least two electrically conductive elements disposed on said first surface of said insulative element and separated from each other by a conductor-free region on said first surface of said insulative element, each of said electrically conductive elements being connected to a respective one of said insulated conductors, the conductor-free region defining a hinge about which the electrode portion is caused to bend by deformation forces encountered during implantation from a substantially planar orientation in a relaxed state to a folded, springy orientation, said springy orientation causing said electrode to return to said substantially planar configuration when said deformation forces are removed.

10. The electrode device of claim 9, further comprising a terminal pin at a proximal end of said lead, each of said insulated conductors electrically connected to said terminal pin.

11. The electrode device of claim 9, wherein said at least two conductive elements are substantially coplanar when said electrode portion is in the substantially planar orientation.

12. The electrode device of claim 11, wherein said electrode portion may bend through approximately 180 degrees such that said at least two electrically conductive elements are substantially parallel to one another in the folded orientation.

13. A method for implanting a cardioversion/defibrillation patch electrode comprising at least two conductive elements disposed on an insulative backing element and separated from each other by a conductor-free region of the insulative backing, the conductor-free region defining a hinge about which the electrode may preferentially bend from a substantially planar orientation in a relaxed state to a folded, springy orientation, the method comprising the steps of:
   bending the electrode about the conductor-free region of the insulative backing to cause the electrode to adopt the folded, springy orientation without deforming said at least two conducting elements;
   inserting the electrode into an introducing means;
   guiding the introducing means to a region near the surface of the heart; and
   forcing the electrode out of the introducing means such that the electrode springily unfolds to adopt the substantially planar orientation without deforming said conducting elements.

14. A cardioversion/defibrillation patch electrode assembly comprising:

an insertable thoracoscopic tube; and
an electrode folded within said insertable thoracoscopic tube, the electrode further comprising:
  an insulative element having first and second opposing surfaces; and
  at least two electrically conductive elements disposed on said first surface of said insulative element and separated from each other by a conductor-free region of said first surface of said insulative element, said conductor-free region defining a hinge about which the electrode is caused to bend from a folded, springy orientation within the insertable thoracoscopic tube to a substantially planar orientation in a relaxed state outside said insertable thoracoscopic tube.

* * * * *